United States Patent [19]

Fehder

[11] Patent Number: 4,994,117
[45] Date of Patent: Feb. 19, 1991

[54] QUANTITATIVE CARBON DIOXIDE DETECTOR

[76] Inventor: Carl G. Fehder, 147 Bradford Ct., Mount Laurel, N.J. 08054

[21] Appl. No.: 175,881

[22] Filed: Mar. 31, 1988

Related U.S. Application Data

[63] Continuation-in-part of Ser. No. 136,600, Dec. 22, 1987, which is a continuation of Ser. No. 896,360, Aug. 13, 1986, Pat. No. 4,728,499.

[51] Int. Cl.$^5$ .................. G01N 31/22; A61M 16/00
[52] U.S. Cl. ................... 436/133; 128/207.14; 422/56; 422/57; 422/58; 422/85; 422/86; 422/88; 436/167; 436/169
[58] Field of Search .......... 422/56, 57, 58, 59, 422/60, 85, 86, 88; 128/207.14; 436/133, 167, 169

[56] References Cited

U.S. PATENT DOCUMENTS

| | | | |
|---|---|---|---|
| 2,880,072 | 3/1959 | Grosskopf | 436/133 |
| 2,890,177 | 6/1959 | Kilmer | |
| 3,068,073 | 12/1962 | Stanford | |
| 3,114,610 | 12/1963 | Gafford et al. | |
| 3,507,623 | 4/1970 | McConnaughey | 422/86 |
| 3,754,867 | 8/1973 | Guenther | |
| 4,003,709 | 1/1977 | Eaton et al. | 422/86 |
| 4,389,372 | 6/1983 | Lalin | 422/86 |
| 4,654,309 | 3/1987 | Mlinar et al. | 422/56 X |
| 4,691,701 | 9/1987 | Williams | |
| 4,728,499 | 3/1988 | Fehder | 422/56 |

FOREIGN PATENT DOCUMENTS 1007525 5/1957 Fed. Rep. of Germany.
1043988 9/1966 United Kingdom.

OTHER PUBLICATIONS

P. K. Birmingham et al "Esophageal Intubation" Anesth. Analg. 1986,65,866-91.

Primary Examiner—Robert J. Warden
Assistant Examiner—Jill Johnston
Attorney, Agent, or Firm—William E. Pelton

[57] ABSTRACT

A detector for rapid response, quantitative determination of carbon dioxide in a gas comprising one or more components, each of which comprises a carrier with a surface to be exposed to the gas, said surface including ane indicating element of a predetermined sensitivity which gives a rapid response signal when exposed to a given concentration of carbon dioxide, the response signals produced when the component or components are exposed to the gas providing a rapid and progressive quantitative determination of the concentration of carbon dioxide or any change with time of said concentration in the gas.

35 Claims, 1 Drawing Sheet

QUANTITATIVE CARBON DIOXIDE DETECTOR

CROSS-REFERENCES TO RELATED APPLICATIONS

This is a continuation-in-part of patent application Ser. No. 136,600 filed Dec. 22, 1987 which is a continuation of Ser. No. 896,360 filed Aug. 13, 1986, now U.S. Pat. No. 4,728,499.

FIELD OF THE INVENTION

This invention relates to a detector for the quantitative determination of carbon dioxide in a gas. The invention is also concerned with a method for determining the concentration of carbon dioxide in a gas, preferably by visual means, which provides a quantitative measurement of said concentration.

BACKGROUND OF THE INVENTION

In U.S. Pat. No. 4,728,499 and the continuation thereof, the disclosure of which is incorporated herein by reference, there is disclosed a combination rapid response device for the detection of carbon dioxide in a concentration of more than 2% in a gas mixture which includes an indicating element, comprising a chromogenic pH-sensitive indicator and other substances, which indicating element provides a visual color change within 5 to 20 seconds when the concentration of carbon dioxide in the gas under investigation is 2% or more. In the preferred embodiment of the device said indicating element is impregnated on to a carrier to form an indicator component which is mounted within an enclosure having an inlet, an outlet and a transparent window through which the component and any color change thereof may be viewed.

Thus, according to U.S. Pat. No. 4,728,499, the nature and concentration of the substances in the indicating element give a rapid, positive color change when the concentration of carbon dioxide in the surrounding gas reaches or exceeds a minimum concentration of 2%, thereby providing a device which enables the positioning of an endotracheal tube in a patient to be determined accurately and rapidly.

However, there are some instances wherein it is necessary to determine more quantitatively the concentration of carbon dioxide in a gas, not merely a given minimum concentration. Also, it is advantageous to have a device and method which provides on-line, real time, repetitive measurement so that temporal changes in carbon dioxide concentrations may be detected.

It has now been found that these further objectives may be achieved by extending the visual detection concept utilized in the device of U.S. Pat. No. 4,728,499 to (i) a component capable of giving progressively different response signals or (ii) a sequential array of components, each of which is pre-calibrated to give a rapid response signal, for example a visual response (color change); each of said response signals in either embodiment corresponding to a different pre-determined concentration of carbon dioxide in the gas under investigation, said embodiment being capable of responding repetitively to changing concentrations of carbon dioxide.

SUMMARY OF THE INVENTION

According to the present invention there is provided a detector for the quantitative determination of carbon dioxide in a gas which comprises a plurality of components in which each component comprises a carrier with a surface to be exposed to the gas, said surface including an indicating element of a predetermined sensitivity which gives a rapid response signal when exposed to a given concentration of carbon dioxide, said components being arranged in a sequence wherein said predetermined sensitivity of indicating element in each component in the sequence differs progressively by an increment which gives a rapid response signal different from that of the indicating element in each preceding component, each of said differing response signals corresponding to a particular concentration of carbon dioxide, said sequence of components thereby providing a progressive quantitative determination of carbon dioxide in the gas, and being capable of responding repetitively, with respect to time, to changing concentrations of carbon dioxide.

The active ingredient of the indicating element, herein referred to as "indicator", which provides the required rapid response signal when exposed to a given concentration of carbon dioxide may be any state of the art indicator which is sensitive to the presence of carbon dioxide and is capable of being calibrated as herein described to give a response signal corresponding to a given predetermined concentration of carbon dioxide. The signal may be visual, e.g. a change in color, or electrical or electronic. Indicators which provide a color change in the presence of carbon dioxide include chromogenic pH-sensitive indicators and oxidation/reduction indicators.

The preferred indicators used in the detector of the present invention are chromogenic pH-sensitive indicators of the type disclosed in U.S. Pat. No. 4,728,499 and the invention will be further described hereinafter with reference to these preferred indicators.

Accordingly, the present invention also provides a detector for the quantitative determination of carbon dioxide in a gas which comprises a plurality of components in which each component comprises a carrier with a surface to be exposed to the gas, said surface being impregnated with a chromogenic indicating element of a predetermined sensitivity which gives a rapid visual color change when exposed to a given concentration of carbon dioxide, said components being arranged in a sequence wherein said predetermined sensitivity of indicating element in each component in the sequence differs progressively by an increment which gives a color change different from that of the indicating element in each preceding component, each of said differing color changes corresponding to a particular concentration of carbon dioxide, said sequence of components thereby providing a progressive quantitative determination of carbon dioxide in the gas and being capable of responding repetitively, with respect to time, to changing concentrations of carbon dioxide.

There are certain indicators, which may be chromogenic, electrical or electronic, which are capable of giving changing signals dependent upon different concentrations of carbon dioxide in the surrounding gas. For example, a chromogenic chemical indicator may progressively change color through different visually distinct colors or shades of color as the concentration of carbon dioxide increases and if the gradation of color or color shades is sufficiently distinct to yield meaningful rapid response signals when compared with an appropriate color comparison chart then a modified detector according to the invention may comprise a single, multi-response component, rather than a plurality of components each of which gives a distinct different response signal. When using a chromogenic chemical indicator, not only the single multi-response component embodiment but also the multi-component embodiment normally will be used with an appropriate color comparison chart.

Thus the present invention further provides a modification of the detector as described above for the quantitative determination of carbon dioxide in a gas, which comprises a component comprising a carrier with a surface to be exposed to the gas, said surface including an indicating element having the capability of providing a plurality of distinguishable rapid response signals upon exposure to progressively changing concentrations of carbon dioxide, each of said signals corresponding to a particular concentration of carbon dioxide, and pre-calibrated comparison means for interpreting said signals.

In a preferred embodiment of the modified detector according to the invention the component comprises a carrier with a surface to be exposed to the gas, said surface being impregnated with a chromogenic indicating element which gives a plurality of rapid visual color or color shade changes upon exposure to progressively changing concentrations of carbon dioxide, each of said colors or color shades corresponding to a particular concentration of carbon dioxide. A precalibrated color comparison chart is provided to interpret the differing colors or color shades.

The invention still further provides a method for the quantitative determination of the concentration of carbon dioxide in a gas which comprises bringing said gas into contact with a surface of one or more components in a detector comprising said component or components wherein the component or each component comprises a carrier with said surface to be exposed to said gas, said surface being impregnated with a chromogenic indicating element of a predetermined sensitivity which, in the case of a single component, gives a series of rapid visual color changes corresponding to varying concentrations of carbon dioxide, or in the case of a plurality of components, gives a rapid visual color change when exposed to a given concentration of carbon dioxide, said plurality of components being arranged in a sequence wherein said predetermined sensitivity of indicating elements in each component in the sequence differs progressively by an increment which gives a color change different from that of the indicating element in each preceding component, and comparing said series of rapid visual color changes or said different color changes with the colors in a precalibrated color comparison chart, thereby obtaining a progressive quantitative determination of the concentration or change in concentration of carbon dioxide in the gas.

DETAILED DESCRIPTION OF THE INVENTION

The preferred embodiment of the detector of the present invention utilizes the same concept for measurement of end-tidal carbon dioxide as that disclosed in U.S. Pat. No. 4,728,499 and retains the rapid response characteristics vital for medical applications but, additionally, by modifying the indicating entity to comprise a component or a plurality of components, each sensitive to different concentrations of carbon dioxide in the surrounding gas, the present detector or modified detector allows the detection of temporal changes in the carbon dioxide concentration and quantitative measurement thereof.

Preferably the indicating element used in the detector of the present invention comprises an aqueous solution of a colorless compound which provides an alkaline solution, i.e. a base, a chromogenic pH-sensitive indicator and a hygroscopic, colorless, transparent, water-miscible liquid, and the sensitivity of the indicating element in each of said components is established by varying the concentration or nature of the base, the concentration or nature of the chromogenic pH-sensitive indicator or any combination of these parameters.

As used herein the term "indicating element" is intended to mean that entity within each component of the detector which provides a rapid response signal, preferably a color change, dependent upon a given concentration of carbon dioxide. The preferred "indicating element" includes at least one "indicator" which is defined herein to include a chemical compound or mixture of compounds, or a suitable electrical or electronic device.

When the indicator is a chemical compound it is usually a chromogenic pH-sensitive indicator which will provide a color change upon exposure to a given concentration of carbon dioxide in the presence of other ingredients of the element which provide the appropriate chemical conditions to induce the required color change. When the indicator is an electrical or electronic device it may be an electrode or transistor which is adapted to detect and measure changes in the ambient chemical parameters induced by the presence of critical amounts of carbon dioxide.

When the response signal provided by the indicating element is a color change, the term "indicator" is intended to mean the actual chemical compound which provides a rapid color change relative to the concentration of carbon dioxide. In this embodiment, the preferred indicator is a chromogenic pH-sensitive indicator i.e. a compound, or mixture of compounds, which rapidly changes color when there is a change in pH in the surrounding medium. For such an indicator to be capable of giving a determination of carbon dioxide it has to be used in combination with a suitable base which provides an alkaline solution. The hydroxyl ions or amine residues present in said alkaline solution react chemically with carbon dioxide to produce a carbonate, bicarbonate and/or carbamate moiety. As described in U.S. Pat. No. 4,728,499, the resulting reaction depletes the hydroxyl ion or amine at the interface and thus lowers the pH at the surface of the component impregnated with the indicating element. The lowering of the pH causes a color change in the indicator.

Since carbon dioxide will not react with the base without water, the presence of a certain minimum amount of water is necessary for the indicating element to provide the required color change. Accordingly, the indicating element also should include a substance which ensures that the required minimum amount of water is present when the detector is used. The preferred substance is a hygroscopic, colorless, transparent, water-miscible liquid.

Thus, a particularly preferred embodiment of the invention is a detector as described above in which said indicating element comprises an aqueous solution of a base, a chromogenic pH-sensitive indicator and a hygroscopic, colorless, transparent, water-miscible liquid, and the sensitivity of the indicating element in each of said components is established by varying the concentration or nature of the base, the concentration or nature of the chromogenic pH-sensitive indicator or any combination of these parameters.

Preferred indicators which may be used in the detector of the present invention include the chromogenic pH-sensitive indicators disclosed in U.S. Pat. No. 4,728,499, namely: metacresol purple, thymol blue, cresol red, phenol red, xylenol blue, a 3:1 mixture of cresol red and thymol blue, bromthymol blue, neutral red, phenolphthalein, rosolic acid, α-naphtholphthalein and orange I. Examples of other indicators which may be used in the detector of the present invention include bromcresol purple, bromphenol red, p-nitrophenol, m-nitrophenol, curcumin, quinoline blue, thymolphthalein and mixtures thereof.

Particularly preferred indicators are metacresol purple, cresol red, bromthymol blue and a mixture of cresol red and bromthymol blue.

The other ingredients of the indicating element in the preferred embodiments of the invention are a base, which is a colorless compound which provides an alkaline solution with water, and a hygroscopic, high-boiling, transparent, colorless, water-miscible liquid.

The base should be a compound whose reaction product with carbon dioxide is water-soluble and which will attain reasonable equilibrium or steady state conditions with carbon dioxide. Suitable bases include sodium carbonate, lithium hydroxide, sodium hydroxide, potassium hydroxide, potassium carbonate, sodium barbitol, tribasic sodium phosphate, dibasic sodium phosphate, potassium acetate, monoethanolamine, diethanolamine and piperidine. A particularly preferred base is sodium carbonate.

The third ingredient in the preferred embodiment of the invention is a hygroscopic, high-boiling, transparent, colorless, water-miscible liquid. The purpose of this ingredient is to entrap sufficient water in the indicating element of each component to enable the exposed surface of the element to act as a reaction zone with the surrounding gas.

An important criterion of each component of the detector according to the invention is that the indicating element be immobilized in or on the carrier. This requires active drying or blotting of the impregnated carrier to achieve minimal moisture retention so as to prevent migration or flow of material while in use. However, since carbon dioxide will not react with the base without water, the presence of a certain minimum amount of water is necessary for the component to work. The hygroscopic liquid ensures that the required minimum amount of water is present in the indicating element when exposed to the gas under investigation.

Examples of suitable hygroscopic liquids for use in the detector of the invention are glycerol, propylene glycol, monoethylene glycol, diethylene glycol, polyethylene glycol and various aliphatic alcohols. Because they are non-toxic and have antiseptic properties which inhibit bacterial and fungal growth, glycerol and propylene glycol or mixtures thereof are particularly preferred.

Each component of the preferred detector according to the invention comprises a carrier with a surface to be exposed to the gas under investigation and said surface is impregnated with an indicating element as described above. The carrier may be made of any material capable of being impregnated with the indicating element and of exhibiting the required sensitivity to carbon dioxide when so impregnated. Preferably the carrier is a bibulous material, such as filter paper or fibrous synthetic material. However, the carrier may be any solid material having no inherent acid or basic properties and to which said indicating element may be impregnated, for example certain porous plastics, in the form of thin films or beads, and inorganic crystals. The carrier is usually impregnated with the indicating element by applying the latter in the form of an aqueous solution and drying or blotting to remove excess moisture, as described in U.S. Pat. No. 4,728,499.

In the multi-component embodiment of the detector according to the invention the components are arranged sequentially according to carbon dioxide sensitivity so that when the detector is exposed to the gas to be tested a quantitative determination of the concentration of carbon dioxide in the gas (if any), is given by a change in color of that component which is calibrated to change color when the concentration is a predetermined amount greater than that indicated by components which have already changed color but less than that which would be indicated by components which have not changed color. The increments of calibration may be chosen according to the accuracy desired. Normally increments of 1.0 to 2.0% are sufficient for most purposes. Also the detector normally is calibrated so that the last one or two components do not change color under the expected test conditions.

The actual configuration of the sequence of components is not critical, provided the response can be easily viewed and interpreted. Preferably, for ease of operation, the components are arranged sequentially in a strip form. If the carrier is a bibulous material, such as filter paper, the components may be formed by applying the indicating element in strips to a single sheet of the carrier material wherein each strip is separated from each adjacent strip by a thread of hydrophobic material to prevent migration of the indicating element from one strip to another. Alternatively, each component may be a separate strip of carrier material impregnated with an indicating element of the required sensitivity and the detector is made up by mounting each strip sequentially on a suitable support, for example a cylindrical spool such as that used in the device of U.S. Pat. No. 4,728,499.

Each of the components in the detector is calibrated by selecting one or more of three parameters of the indicating element, namely:
1. the nature of the base;
2. the concentration of the base in the solution used to impregnate the carrier. This parameter provides the initial pH of the solution in equilibrium or steady state with the baseline concentration of carbon dioxide; and
3. the pK of the chromogenic pH-sensitive indicator.

The critical factors for calibration are:
(a) the difference between the initial pH and the pK of the indicator and
(b) the new equilibrium or steady state pH of the particular indicating element at the specific carbon dioxide concentration of interest for the particular base used in the indicating element.

By utilizing a plurality of components each with an indicating element of different initial pH to pK spread calibrated to a different concentration of carbon dioxide, i.e. different equilibrium or steady state pH, it is possible to precisely quantitate the concentration of carbon dioxide present in the test gas at any point in time and to detect changes of carbon dioxide concentration with time. Thus, the detector is capable of responding repetitively to changing concentrations of carbon dioxide.

Precision will depend upon the number of components and the magnitude of color variation exhibited by each indicator around its pK when subjected to small variations in pH which will translate to the incremental color change in the indicating element of each adjacent component. Precision also depends upon the choice of detector to exhibit a suitable response according to the range of concentration of carbon dioxide in the test gas.

The indicating element in each component will respond to a specific concentration range of carbon dioxide since the color change in the transition pH range of the indicator will be continuous with small changes in pH.

Color comparison charts for a variety of known carbon dioxide concentrations will provide rapid quantitation of unknown carbon dioxide concentrations in a gas provided the gas is known not to contain other acidic gases, such as sulfur dioxide or hydrogen sulfide, which would interfere with the measurement.

When the components of the detector are in the form of a sequence of strips as described above, said components may be mounted on a spool supported within a transparent enclosure in a device such as that described and illustrated in U.S. Pat. No. 4,728,499.

The preferred embodiment of the device disclosed in U.S. Pat. No. 4,728,499 provides a convenient and comparatively simple device for obtaining a rapid and substantially fool-proof indication of the proper or improper placement of an endotracheal catheter in the trachea of a patient, particularly an apneic patient.

Accordingly, said preferred embodiment includes an indicating element which responds positively and rapidly to the presence of a certain concentration of carbon dioxide, i.e. the amount of carbon dioxide which is present in the exhaled breath of a human being. This concentration is normally of the order of 4.5–5.0%, but possibly may be as low as 2%.

However, although an extremely rapid response, of the order of 5 to 20 seconds, is crucial for the successful operation of said device, it is equally important that the indicating element should not be so sensitive that it changes color too quickly when exposed to an atmosphere containing some minimal amount of carbon dioxide, for example, ambient air which normally contains about 0.03% carbon dioxide, which minimal amount is substantially less than that present in exhaled breath.

Accordingly, the indicator used in the device according to U.S. Pat. No. 4,728,499 is selected so that it does not change color instantaneously upon exposure to an atmosphere which contains a certain minimum amount of carbon dioxide, for example, ambient air, and the resultant delay provides the operator with ample time to open the package in which the device is sealed and connect the device to an endotracheal catheter after having placed the catheter in the patient's throat and having inflated the sealing cuff on the catheter.

Since the exposed indicator may eventually change color upon continued exposure to ambient air, or any atmosphere containing minimal amounts of carbon dioxide, because even a slow rate of diffusion of carbon dioxide into the indicator zone will lead, in time, to a sufficient depletion of base to cause a color change, the device is normally enclosed in atmospheric sealing means which is constructed to be opened immediately prior to use of said device.

Similar considerations apply to the detector of the present invention, particularly when it is calibrated to be used for the monitoring of carbon dioxide concentrations in conjunction with an endotracheal tube, an anesthesia mask or a resuscitation mask.

A preferred atmospheric sealing means for storing the detector is a gas impermeable metallic foil.

If a hydrophilic filter is included at the proximal end of the device, the device may be attached to an endotracheal tube, anesthesia mask or resuscitation mask or to the exhaust port of a resuscitation bag for extended periods of time, thereby providing breath to breath quantitation of end-tidal carbon dioxide and detection of changes in this parameter with time under varying physiological conditions.

If the device is attached to the expiratory port of a resuscitation bag the filter may be unnecessary.

Preferably the filter comprises a porous or fibrous bibulous material impregnated with a hydrophilic liquid, such as glycerol or propylene glycol. The presence of such a filter ensures that minimal water vapor in exhaled breath will not condense within the device and the filter thus prevents leaching of the ingredients of the indicating element from its carrier.

The hydrophilic filter may include a porous hydrophobic membrane, made from a material such as foamed polyethylene or styrofoam, attached to the distal end of the filter just inside the inlet of the device. The filter, without or with the membrane, should offer minimal resistance to gas flow up to 100 l/min.

The surface of the multi-component detector may be coated with a water-repellant film of a carbon dioxide-permeable material to augment resistance to leaching by condensed water droplets. Preferred materials are silicone and fluorocarbons. The specific material used should have no significant effect on the pH of the indicator element.

In another embodiment of the invention the components containing the indicator elements may be enveloped in or laminated with a polymeric film which is water resistant, transparent and is permeable to carbon dioxide. Examples of such polymeric films are ultra thin films of cellulose butyrate or linear low density polyethylene. The presence of the film extends the response time and this embodiment would be used only when a rapid response time, i.e. a response time of 5 to 20 seconds, is not critical. However, the embodiment is still useful for many applications wherein a longer response time, of the order of 20 to 30 seconds or more, is tolerable.

Attachment of the detector to the exhaust port of a resuscitation bag, as described hereinabove, obviates the concern regarding leaching of chemicals from the indicating element, since in this embodiment the entire detector is physically separated from the patient's trachea by valves.

The following Examples illustrate the preparation of the indicating element and component used in the detector according to the invention.

EXAMPLE 1

In this Example the indicating element for each component is prepared from an aqueous solution of sodium carbonate as the base, meta cresol purple as the chromogenic pH-sensitive indicator and glycerol as the hygroscopic liquid.

For each component the amount of indicator and glycerol is kept constant while the amount of base is varied to provide the desired response characteristic.

Four components are prepared from the following indicating elements

| Strip No. | Sodium carbonate $10^{-2}$ M | Meta cresol purple % w/v | Glycerol % by volume |
| --- | --- | --- | --- |
| 1. | 1.0 | 0.15 | 50 |
| 2. | 1.26 | 0.15 | 50 |
| 3. | 1.58 | 0.15 | 50 |
| 4. | 2.0 | 0.15 | 50 |

The four components are made up by immersing strips of Whatman No. 1 filter paper in aqueous solutions of the above indicating elements until they are fully impregnated with the solution. The strips are blotted until no further solution can be expressed therefrom and they are then assembled in order of increasing base concentration and affixed to a support, for example of cardboard or celluloid. The support is mounted in an appropriate enclosure or chamber wherein it is exposed to gases containing varying concentrations of carbon dioxide. A progressive change in color in each strip is observed dependent upon the concentration of carbon dioxide in the gas until the concentration reaches the saturation point for these particular indicating elements. The results are set out in the following Table 1.

TABLE 1

| Concentration of Carbon Dioxide | COLOR | | | | Remarks |
| --- | --- | --- | --- | --- | --- |
| | Strip 1 | Strip 2 | Strip 3 | Strip 4 | |
| .03% | purple | purple | purple | purple | No color change |
| .50% | grayish-yellow | yellowish-grey | grey | dull fuschia | |
| 1.00% | golden yellow | dirty yellow | dirty yellow | grayish-yellow | |
| 1.50% | light yellow | golden yellow | golden yellow | dirty yellow | |
| 2.00% | light yellow | golden yellow | golden yellow | golden yellow | |
| 2.50% | light yellow | light yellow | light yellow | light yellow | Saturation |

By comparing the above results with a pre-calibrated standardized color chart the concentration of carbon dioxide in the surrounding gas at any given time may be determined.

EXAMPLE 2

A three-component detector is prepared from aqueous solutions of the following indicating elements:

| Strip No. | Base | Indicator w/v | Glycerol % by volume |
| --- | --- | --- | --- |
| 5. | $1.5 \times 10^{-2}$ M sodium carbonate | 0.22% metacresol purple | 50 |
| 6. | $1.5 \times 10^{-2}$ M sodium carbonate | 0.1% cresol red + 0.18% bromthymol blue | 50 |
| 7. | $1.0 \times 10^{-2}$ M sodium carbonate | 0.24% bromthymol blue | 50 |

The above indicating elements are impregnated on to porous hydrophlic polyethylene foam 0.0625 inch thick (Porex DBE polyethylene foam-fine pore).

The elements were assembled to form a detector in a manner similar to that described in Example 1 and this detector was exposed to gases containing varying amounts of carbon dioxide. The results are shown in Table 2.

TABLE 2

| Concentration of Carbon Dioxide | COLOR | | |
| --- | --- | --- | --- |
| | Strip 5 | Strip 6 | Strip 7 |
| .03% | purple | blue violet | light blue |
| 1.00% | greyish-purple | light blue | NO CHANGE |
| 2.00% | greyish-yellow | blue grey | NO CHANGE |
| 3.00% | dirty yellow | grey | lighter blue |
| 4.00% | dark yellow | dark green | grey |
| 5.00% | golden yellow | green | greenish grey |
| 6.00% | lighter yellow | yellow green | dirty green |
| 7.00% | bright yellow | greenish yellow | green |
| 8.00% | NO CHANGE | dark yellow | lighter green |
| 9.00% | NO CHANGE | golden yellow | greenish-yellow |
| 10.00% | NO CHANGE | lighter yellow | dark yellow |

Again, a quantitative determination of the carbon dioxide concentration for each gas is obtained by comparing the above results with a pre-calibrated standardized color chart.

EXAMPLE 3

This Example illustrates a modified detector according to the invention comprising a single component with an indicating element which provides a plurality of distinguishable color changes when exposed to varying concentrations of carbon dioxide.

Strip 4 of Example 1 is used to illustrate this embodiment. This strip comprises a strip of Whatman No. 1 filter paper impregnated with an indicating element formed from an aqueous solution of $2.0 \times 10^{-2}$ M sodium carbonate, 0.15 w/v meta cresol purple and 50% by volume glycerol.

The strip is mounted as described in Example 1 and exposed to gases containing increasing concentrations of carbon dioxide from 0.03% (normal ambient air) to 2.50%. The results are the same as given in Table 1. Comparison of the changing shades of color against a standardized color chart give similar information to that obtained in Example 1. Thus, technically, the single component detector of this Example is comparable to the multi-component detector illustrated in Example 1 and such single component detector is certainly within the scope of the invention. However, in practice, the fine gradations of color shade for differing concentrations of carbon dioxide require very careful color comparison against the precalibrated chart and the multi-component detector of Example 1 is therefore preferred.

BRIEF DESCRIPTION OF THE DRAWINGS

A preferred embodiment of the invention is a multi-component detector in which each component is an impregnated strip of bibulous material mounted on a support spool in a device similar to that described and illustrated in U.S. Pat. No. 4,728,499. The invention will now be further described with reference to the accompanying drawings in which.

DETAILED DESCRIPTION OF THE DRAWINGS

Figure 1:
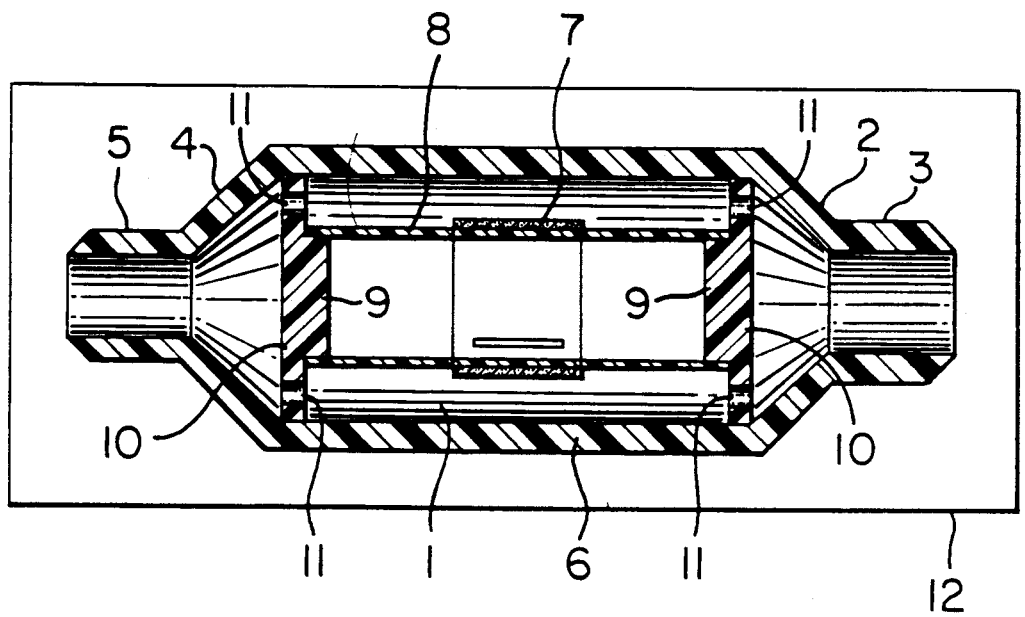
FIG. 1 is a side cross-section of a simplified version of the device of U.S. Pat. No. 4,728,499 and the modified detector of the present invention.

The device illustrated in FIG. 1 of the drawings comprises a cylindrical housing 1 having at its proximal end a cone-shaped coupling 2 terminating in a cylindrical connector 3 and at its distal end a cone-shaped coupling 4 terminating in a cylindrical connector 5.

The cylindrical housing 1 is made from a clear, colorless, transparent plastic, for example, an acrylic polymer, such as that available under the Trademark PLEXIGLAS, polymethyl acrylate, polymethyl methacrylate, polycarbonate, polystyrene or styrene-acrylonitrile copolymer.

The combination of housing and coupling/connector units effectively forms an enclosure having an inlet formed by proximal connector 3 and an outlet formed by distal connector 5.

The clear transparent plastic used for the cylindrical housing provides an effective window 6 for viewing the indicator component 7, which comprises a strip of filter paper impregnated with an appropriate indicating element. Fogging of said window by the humidity in exhaled breath is prevented by coating the inner surface of the window with a suitable anti-fogging surfactant, such as diotyl sodium sulfosuccinate.

The indicator strip 7 is securely wrapped around a cylindrical spool which is made from a rigid plastic, such as polyethylene. The spool 8 is mounted at each end on an inwardly facing flange 9 of a support 10.

The supports 10 are substantially circular in shape and have a plurality of apertures 11 which allows substantially unrestricted flow of gas through the device when in use.

The spool supports 10 are preferably made from a clear plastic, similar to that used for the cylindrical housing.

The device is preferably enclosed within atmospheric sealing means, for example a gas-impermeable metal foil 12, until required for use.

Figure 2:
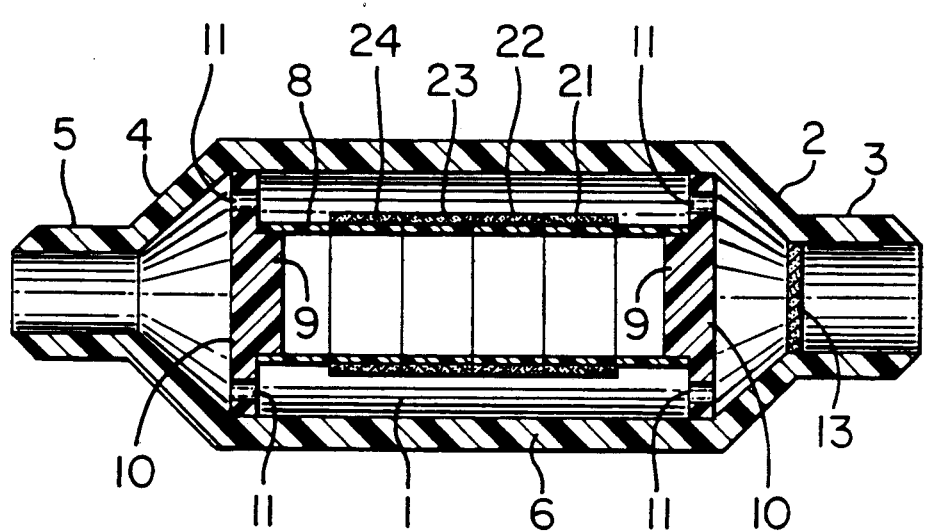
FIG. 2 is a similar view of the device of FIG. 1 but with the single rapid response strip replaced by a multicomponent detector according to the present invention.

FIG. 2 illustrates a detector according to the present invention mounted on a spool 8 in a device similarly to that illustrated in FIG. 1.

In this embodiment the single indicator strip 7 is replaced by four strips 21, 22, 23 and 24 impregnated, respectively, with the indicating elements 1, 2, 3 and 4 of Example 1 herein.

The resulting device may be connected to an endotracheal tube through connector 3 and be used to obtain quantitative determinations of the carbon dioxide concentration in the exhaled breath of a patient over a given time. If desired, a hydrophilic filter 13 as described above may be included in the device.

It is a characteristic of the present invention that the response time of each indicator element is comparable to that of the device disclosed in U.S. Pat. No. 4,728,499. Thus each indicating element normally will give a rapid response signal corresponding to the concentration of carbon dioxide to which it is sensitive within 5 to 20 seconds after being exposed to the gas. Possible exceptions are when the element is coated with a water-repellent film or is enveloped in a polymeric film, as described above, when the response time might be somewhat extended. However, even in these embodiments the response time, of the order of 20 to 30 seconds or more, is sufficiently fast for many applications. Of course, such an embodiment should not be used when a rapid response time is critical.

I claim:

1. A detector for the quantitative determination of the concentration of carbon dioxide contained in a gas sample, the detector comprising a plurality of indicator elements supported by at least one support component, each of said indicator elements producing a distinguishable signal within a rapid response time, each such signal corresponding to a predetermined different concentration of carbon dioxide in the gas sample, said indicator elements being arranged in a sequence wherein each signal of each of said indicator elements corresponds in turn to a progressively different concentration of carbon dioxide from that to which the signal of each preceding indicator element corresponds, said sequence of components thereby providing a progressive quantitative determination of carbon dioxide in the gas sample.

2. The detector according to claim 1 for the quantitative determination of the concentration of carbon dioxide in a gas sample, comprising in addition comparison means for converting each of said signals to a representation of the quantity of carbon dioxide contained in the gas sample.

3. A detector according to claim 1, in which each of said indicator elements comprises in combination an aqueous solution of a base, a chromogenic pH-sensitive indicator and a hygroscopic, colorless, transparent, water-miscible liquid, the relative concentrations of which are predetermined to produce said distinguishable signal within a rapid response time when exposed to a selected concentration of carbon dioxide in said gas sample.

4. The detector according to claim 3, in which said chromogenic pH-sensitive indicator is selected from the group consisting of metacresol purple, thymol blue, cresol red, phenol red, xylenol blue, a 3:1 mixture of cresol red and thymol blue, bromthymol blue, neutral red, phenolphthalein, rosolic acid, $\alpha$-naphtholphthalein, orange I, bromcresol purple, bromphenol red, p-nitrophenol, m-nitrophenol, curcumin, quinoline blue, thymolphalein and mixtures thereof.

5. The detector according to claim 3, in which said base is selected from the group consisting of sodium carbonate, lithium hydroxide, sodium hydroxide, potassium hydroxide, potassium carbonate, sodium barbitol, tribasic sodium phosphate, dibasic sodium phosphate, potassium acetate, monoethanolamine, diethanolamine and piperidine.

6. The detector according to claim 3, in which said hygroscopic liquid is selected from the group consisting of glycerol, propylene glycol, monoethylene glycol, diethylene glycol, polyethylene glycol and mixtures thereof.

7. The detector of claim 3 in which each of said indicator elements is impregnated within a carrier element on said component.

8. The detector of claim 7 in which said carrier element consists of bibulous material.

9. The detector according to claim 8, in which said carrier element is filter paper, a sheet of fibrous synthetic material or a film of porous plastic.

10. The detector according to claim 8, in which said bibulous material is a porous hydrophilic polyethylene foam.

11. The detector according to claim 1, in which there are four of said indicator elements each of which is formed from an aqueous solution comprising a different one of:
(1) $1.0 \times 10^{-2}$M sodium carbonate, 0.15% w/v meta cresol purple and 50% by volume glycerol;
(2) $1.26 \times 10^{-2}$M sodium carbonate, 0.15% w/v meta cresol purple and 50% by volume glycerol;
(3) $1.58 \times 10^{-2}$M sodium carbonate, 0.15% w/v meta cresol purple and 50% by volume glycerol; and
(4) $2.0 \times 10^{-2}$M sodium carbonate, 0.15% w/v meta cresol purple and 50% by volume glycerol.

12. The detector according to claim 1, in which there are three of said indicating elements, each of which is formed from an aqueous solution comprising a different one of:
(1) $1.5 \times 10^{-2}$M sodium carbonate, 0.22% w/v meta cresol purple and 50% by volume glycerol;
(2) $1.5 \times 10^{-2}$M sodium carbonate, a mixture of 0.1% w/v cresol red and 0.18% w/v bromthymol blue and 50% by volume glycerol; and
(3) $1.0 \times 10^{-2}$M sodium carbonate, 0.24% w/v bromthymol blue and 50% by volume glycerol.

13. The detector according to claim 1 comprising a single one of said indicating elements impregnated within a carrier of filter paper and formed from an aqueous solution of $2.0 \times 10^{-2}$M sodium carbonate, 0.15 w/v meta cresol purple and 50% by volume glycerol.

14. The detector of claim 1, in which said supporting component is mounted within an enclosure defined by walls and having a transparent window in one of said walls, and an inlet and an outlet, each of said indicating elements being positioned and arranged so as to be viewed through said transparent window.

15. The detector according to claim 14 which also includes atmospheric sealing means for preventing atmospheric contamination of the detector prior to use, said atmospheric sealing means enclosing said enclosure containing each of said indicating elements and being constructed so as to be opened immediately prior to use of the detector.

16. The detector according to claim 15, in which said sealing means comprising an envelope made from a gas-impermeable metallic foil.

17. The detector according to claim 14, in which said transparent window is a clear transparent acrylic polymer.

18. The detector according to claim 17, in which a hydrophilic filter is included at one end of said enclosure.

19. The detector according to claim 18 in which said hydrophilic filter comprises a bibulous material impregnated with glycerol or propylene glycol.

20. The detector according to claim 18, in which said hydrophilic filter includes a porous hydrophobic membrane enclosing said hydrophilic filter.

21. The detector according to claim 1, in which each of said indicator elements is coated with a water-repellent film of a carbon dioxide-permeable material.

22. The detector according to claim 21, in which said carbon dioxide-permeable material is silicone or a fluorocarbon.

23. The detector according to claim 1, in which each of said indicator elements is enveloped in or laminated with a water-resistant, transparent, carbon dioxide-permeable polymeric film.

24. The detector according to claim 23, in which said film is made from cellulose butyrate or linear, low density polyethylene.

25. The detector of claim 1 comprising a plurality of said support components each of said indicator elements being carried by a corresponding one of said support components.

26. The detector of claim 1 in which said indicating elements are mounted substantially side-by-side.

27. The detector of claim 1 in which said distinguishable signal consists of a detectable color.

28. The detector of claim 27 in which said detectable color is visible.

29. The detector of claim 1 in which each of said distinguishable signals is present at a given concentration of carbon dioxide in the gas sample and is not present at a concentration of carbon dioxide in the gas sample which is different from said given concentration.

30. The detector of claim 1 in which each of said indicating elements has a detectable pH.

31. The detector of claim 1 in which said distinguishable signal consists of a given value of said detectable pH.

32. The detector of claim 1, in which said distinguishable signal of each of said indicator elements disappears within a rapid response time after the appearance of said distinguishable signal when the concentration of carbon dioxide in the sample is less than that concentration of carbon dioxide which is sufficient to cause said signal to be produced.

33. A method for the quantitative determination of the concentration of carbon dioxide in a gas which comprises bringing said gas into contact with a surface of at least one component in a detector said at least one component having a carrier defining said surface to be exposed to said gas, said surface being impregnated with a plurality of chromogenic indicating elements of a predetermined sensitivity which produce a series of rapid visual color changes corresponding to varying concentrations of carbon dioxide, said indicating elements being arranged on said surface in a sequence wherein said predetermined sensitivity of each of said indicating elements in the sequence differs progressively by an increment which gives a color change different from that of each preceding indicating element, and comparing said series of rapid visual color changes or said different color changes with the colors in a precalibrated color comparison chart, thereby obtaining a progressive quantitative determination of the concentration or change in concentration of carbon dioxide in the gas.

34. A detector for the quantitative determination of the concentration of carbon dioxide contained in a gas sample, the detector comprising a component having a carrier with a surface to be exposed to the gas, said surface including an indicating element of a predetermined sensitivity to carbon dioxide and which produces a plurality of distinguishable and reversible rapid response signals when exposed to progressively changing concentrations of carbon dioxide, each of said plurality of distinguishable response signals corresponding to a particular concentration range of carbon dioxide and being arranged in a predetermined sequence on said surface thereby providing a progressive quantitative determination of the concentration of carbon dioxide contained in said gas sample.

35. A detector for the quantitative determination of the concentration of carbon dioxide contained in a gas sample, the detector comprising a component having a carrier with a surface to be exposed to the gas sample, said surface being impregnated with a plurality of chromogenic indicating elements each of said indicating elements having a predetermined sensitivity to carbon dioxide and being capable of progressively displaying a plurality of distinguishable colors when exposed to progressively changing concentrations of carbon dioxide within a rapid response time, each of said plurality of distinguishable colors being produced in response to a particular concentration range of carbon dioxide and each of said plurality of chromogenic indicating elements being arranged in a predetermined sequence thereby providing a progressive quantitative determination of the concentration of carbon dioxide contained in said gas.

* * * * *